US006699507B1

(12) United States Patent
Albrecht et al.

(10) Patent No.: US 6,699,507 B1
(45) Date of Patent: Mar. 2, 2004

(54) COLLOIDAL PARTICLES OF DIFFERENT ELEMENT COMPOSITION FOR SPECIFIC LABELING PURPOSES

(75) Inventors: Ralph M. Albrecht, Belleville, WI (US); Daryl A. Meyer, Madison, WI (US); Julian Hillyer, Madison, WI (US)

(73) Assignee: Wisconsin Alulmni Research Foundation, Madison, WI (US)

( * ) Notice: Subject to any disclaimer, the term of this patent is extended or adjusted under 35 U.S.C. 154(b) by 0 days.

(21) Appl. No.: 09/368,764

(22) Filed: Aug. 5, 1999

(51) Int. Cl.⁷ ................................................ A61K 9/14
(52) U.S. Cl. ...................................... 424/489; 424/489
(58) Field of Search ........................... 424/489; 75/0.5; 430/137, 197

(56) References Cited

U.S. PATENT DOCUMENTS

| 3,992,512 | A |   | 11/1976 | Petrow et al. |
|---|---|---|---|---|
| 4,059,541 | A |   | 11/1977 | Petrow et al. |
| 4,102,819 | A |   | 7/1978 | Petrow et al. |
| 4,446,238 | A |   | 5/1984 | De Mey et al. |
| 4,859,612 | A |   | 8/1989 | Cole et al. |
| 4,863,510 | A | * | 9/1989 | Tamemasa et al. ........... 75/0.5 |
| 4,879,220 | A |   | 11/1989 | Mrsny et al. |
| 4,880,751 | A |   | 11/1989 | Georghegan |
| 4,920,059 | A | * | 4/1990 | Moeremans et al. .......... 436/86 |
| 5,034,313 | A | * | 7/1991 | Shuman ...................... 430/616 |
| 5,120,643 | A |   | 6/1992 | Ching et al. |
| 5,204,219 | A | * | 4/1993 | Van Ooij et al. ........... 430/272 |
| 5,248,772 | A |   | 9/1993 | Siiman et al. |
| 5,252,522 | A |   | 10/1993 | Dorbath et al. |
| 5,332,646 | A | * | 7/1994 | Wright et al. ................ 430/137 |
| 5,352,645 | A | * | 10/1994 | Schwartz ..................... 502/262 |
| 5,384,265 | A |   | 1/1995 | Kidwell et al. |
| 5,391,272 | A |   | 2/1995 | O'Daly et al. |
| 5,514,602 | A |   | 5/1996 | Brooks, Jr. et al. |
| 5,521,289 | A |   | 5/1996 | Hainfeld et al. |
| 5,591,903 | A |   | 1/1997 | Vesenka et al. |
| 5,700,639 | A |   | 12/1997 | Trauth et al. |
| 5,714,389 | A |   | 2/1998 | Charlton et al. |
| 5,728,590 | A |   | 3/1998 | Powell |
| 5,753,261 | A |   | 5/1998 | Fernandez et al. |
| 5,779,784 | A |   | 7/1998 | Eadon et al. |
| 5,814,468 | A |   | 9/1998 | Siiman et al. |
| 5,820,879 | A |   | 10/1998 | Fernandez et al. |
| 5,908,736 | A | * | 6/1999 | Yamazaki ..................... 430/351 |

OTHER PUBLICATIONS

H. Bennett "Concise Chemical and Technical Dictionary", p. 759; 1962.*

(List continued on next page.)

Primary Examiner—Thurman K. Page
Assistant Examiner—S. Tran
(74) Attorney, Agent, or Firm—Michael Best & Friedrich LLP; Teresa J. Welch; Jeffrey D. Peterson

(57) ABSTRACT

The invention relates to colloidal particles of differing elemental compositions with differing morphologies, and to methods of preparing same. The invention also provides applications of such colloidal particles as labels in microscopy, as staining agents, and as biomolecule or drug carriers.

14 Claims, 8 Drawing Sheets

OTHER PUBLICATIONS

Ralph M. Albrecht et al., "Correlative video–enhanced light microscopy, high voltage transmission electron microscopy, and field emission scanning electron microscopy for the localization of colloidal gold labels", Immunocytochemistry: A Practical Approach, J. E. Beesley, Oxford University Press, pp. 151–176, 1993.

Julián F. Hillyer et al., "Correlative Instrumental Neutron Activation Analysis, Light Microscopy, Transmission Electron Microscopy, and X–ray Microanalysis for Qualitative and Quantitative Detection of Colloidal Gold Spheres in Biological Specimens", *Microsc. Microanal.*, 4, 481–490, 1999.

S.R. Simmons et al., "Correlative atomic–force microscopy and high–resolution scanning electron microscopy of proteins attached to platelet surfaces", G.W. Bailey and C. L. Rieder, Eds., Proc. $51^{st}$ Annual Meeting of the Microscopy Society of America, pp. 230–231, 1993.

T. C. Green et al., "Monalayer Arrangement of Pt Nanoparticles", *Microsc. Microanal.* 4(Suppl. 2: Proceeding) Microscopy Society of America, pp. 738–739, 1998.

Scott R. Simmons et al., "Optimizing Parameters for Correlative Immunogold Localization by Video–enhanced Light Microscopy , High–voltage Transmission Electron Microscopy, and Field Emission Scanning Electron Microscopy", *The Journal of Histochemistry and Cytochemistry*, vol. 38, No. 12, pp. 1781–1785, 1990.

* cited by examiner

FIG. 2  Bar = 200 nm

Bar = 100 nm

Bar = 50 nm

COLLOIDAL PARTICLES OF DIFFERENT ELEMENT COMPOSITION FOR SPECIFIC LABELING PURPOSES

STATEMENT REGARDING FEDERALLY SPONSORED RESEARCH OR DEVELOPMENT

This invention was made with United States government support under Grant No. HL37351 and ES06085 awarded by the National Institutes of Health. The United States government has certain rights in this invention.

CROSS-REFERENCE TO RELATED APPLICATIONS

Not Applicable

BACKGROUND OF THE INVENTION

This invention relates to colloidal particles of differing elemental compositions with differing morphologies and to methods of preparing same. The invention is particularly well-suited for use of the colloidal particles as labels in microscopy, as staining agents, and as biomolecule or drug carriers.

Colloidal particles have found myriad uses from biology to electronics. Colloidal gold, for example, has found particular use in biological labeling for localization of cell components at the microscopic and the ultrastructural level. In such use, colloidal gold is conjugated to a wide variety of biologically active molecules, i.e., biomolecules, such as antibodies, antibody fragments, ligands, ligand fragments or other molecular species that bind specifically to cellular targets. Colloidal gold particles can be made in sizes ranging from 1–150 nm. Depending on the particle size, colloidal gold is visible, or can be enhanced to be visible, in light microscopy, electron microscopy, x-ray microscopy or scanning force microscopy. Single particles of 10 nm and above are detectable but not resolvable by various types of light microscopy. Larger particles are most useful for applications where ease of detectability is important. Medium sized particles (10–20 nm) are still large enough for single particles to be detected by light microscopy (LM) and are resolvable by scanning electron microscopy (SEM) and transmission electron microscopy (TEM), with particles as small as ~1 nm being detectable by TEM.

The use of colloidal gold particles as cellular markers in multiple labeling applications, however, is problematic. Multiple labeling which compares the localization of one type of label to another requires the use of different sized gold particles. The need to use differently sized particles, whose sizes do not overlap, limits the level of spatial resolution attainable as well as the total number of different cellular targets that can be labeled simultaneously. While smaller-sized particles permit a high degree of spatial resolution, the level of resolution drops rapidly with increasing particle size. This severely limits the precision of co-localization, particularly in the molecular and sub-molecular size ranges.

Thus, a problem, largely unattended in the art, is the lack of colloidal labels that are not dependent upon varying particle size to achieve co-localization and identification of multiple cellular targets. There is a need for smaller particles of differing elemental composition in cases where the path to the structure or molecule to be labeled is obscured by other structures, when the structures to be labeled are small and close together, or when a high particle concentration is necessary to achieve satisfactory labeling density.

BRIEF SUMMARY OF THE INVENTION

The present invention provides a heretofore unmet need for colloidal particles of differing elemental composition with differing morphologies. Colloidal particles of differing shapes are suitably made of several different metals. Differing elemental compositions permit multiple labeling procedures with similarly sized particles. Resolution is thus possible with TEM, SEM in both secondary and backscattered modes, and with force microscopy in constant force, tapping and phase modes. The use of the colloidal particles of the present invention overcomes the limitations of prior art colloidal gold multiple labeling techniques requiring differently sized particles whose sizes do not overlap in spatial resolution, limiting the total number of different cell targets that can be labeled simultaneously.

The foregoing, and other advantages of the present invention, are realized in one aspect thereof in a method of making nonspherical colloidal particles of a metal selected from the group consisting of silver, palladium, platinum, rhodium, molybdenum and ruthenium. The method includes reducing a solution of a compound of the metal with a reducing agent selected from the group consisting of tannic acid, sodium citrate, ferrous sulfate, ascorbic acid, sodium borohydride, hydrogen, ethanol, methanol and combinations thereof. The colloidal particles made from the method of the present invention have morphologies or shapes which are cuboidal, lobate or geodesic. The particles range in size from about 1 nm to about 500 nm, preferably about 3 nm to about 18 nm.

In another aspect, the present invention provides a method of multi-immunolabeling or multiligand labeling which comprises conjugating to each biomolecule sought to be labeled metal colloidal particles in which the colloidal particles for each biomolecule differ in elemental composition or in morphology or a combination of both. The biomolecules are suitably an antibody, a cell, a cellular component, a cellular surface molecule, a protein, an antigen, a nucleic acid or fragment thereof or a drug. The colloidal particles are suitably selected from silver, palladium, platinum, rhodium, molybdenum and ruthenium and have shapes selected from spherical, cuboidal, lobate or geodesic.

In a further aspect, the present invention provides a method of gel staining which comprises staining each species sought to be stained with colloidal metal particles wherein the colloidal particles for each species differ in metal composition and/or particles size. The metals are selected from silver, palladium, platinum, rhodium, molybdenum and ruthenium, and the particle size ranges from about 1 nm to about 100 nm. It has been found that, depending on particle size, platinum and palladium particles are dark amber to golden-brown. Silver particles range in color from red to purple while, rhodium is amber or reddish brown to yellow, and ruthenium particles are orange to yellow orange and molybdenum is blue.

In yet another aspect, the present invention provides an in vivo delivery system, which system includes a biomolecule-carrier particle conjugate for delivering a biomolecule into the body of a subject/host wherein the carrier particles are colloidal particles of a metal selected from gold, silver, palladium, platinum, rhodium, molybdenum and ruthenium, and have a particle size ranging from about 1 nm to about 80 nm; and an administration means for administering the conjugate to the subject/host. The colloidal particles suitably have a morphology which is cuboidal, lobate or geodesic. The biomolecule is suitably a protein, a peptide, an antibody, a nucleic acid or fragments thereof, or a drug or other theraputic substance intended for use in diagnosis, treatment or prevention of a pathological condition.

Other advantages and a fuller appreciation of specific adaptations, compositional variations, and physical attributes will be gained upon an examination of the following detailed description of preferred embodiments, and the appended claims taken in conjunction with the figures of the drawing. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which.

DETAILED DESCRIPTION OF THE INVENTION

The present invention relates to colloidal particles of differing elemental composition and differing morphologies. The particles of the present invention are most particularly adapted for use in molecular and immunolabeling, gel staining and drug or biomolecule delivery. Accordingly, the present invention will now be described in detail with respect to such endeavors; however, those skilled in the art will appreciate that such a description of the invention is meant to be exemplary only and should not be viewed as limitative on the full scope thereof.

The present invention provides colloidal particles of differing elemental composition and methods of preparing same in certain shapes and sizes. Such colloidal particles are of value as labels in microscopy, as staining agents, and as biomolecule carriers. The present invention is especially characterized by an ability to facilitate multiple labeling techniques of, e.g., biostructures within cells, and to facilitate delivery in vivo of biomolecules or drugs. These attributes are achieved through a novel combination of physical features and chemical features.

In the following description of the method of the invention, process steps are carried out at room temperature and atmospheric pressure unless otherwise specified. As used herein, the term "cM" refers to "colloidal metal", e.g., cAg refers to colloidal silver. The term "faceted" refers to morphologies of colloidal particles that have straight edges and sharp corners, e.g., tetrahedral, octahedral, rhomboidal, cuboidal, and multifaceted such as geodesic or soccer balls.

The term "conjugation" is meant to refer to the binding of a metallic colloidal particle to another species, particularly a biomolecule, such as a protein or an antibody, primarily through noncovalent forces, which include but are not limited to adsorption phenomena, hydrophobic interactions and van der Waals attractions. The term "biomolecule" is meant to refer to any biological substance or material such a peptide, protein, antibody, antigen, nucleic acid or biostructure, e.g., cell components, a fragment of any of these, or a therapeutic substance, e.g., a drug or other chemical substance intended for use in diagnosis, cure, treatment or prevention of a pathological condition.

Figure 1:
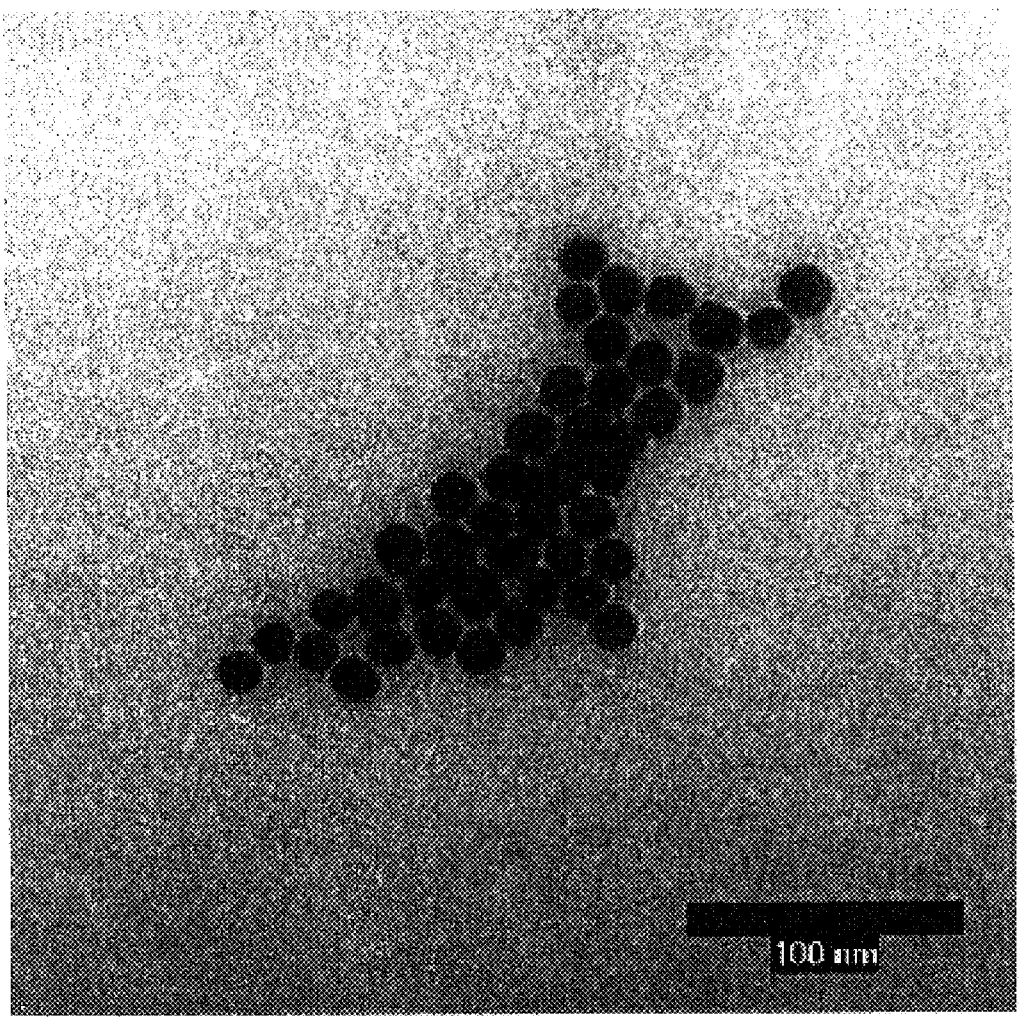
FIG. 1 is a TEM micrograph of spherical cAu particles.

In one aspect, the present invention provides nonspherical colloidal particles of differing elemental composition wherein the element is a metal which suitably includes silver, platinum, palladium, rhodium, molybdenum and ruthenium. The particles of the present invention are distinguishable in shape from prior art colloidal gold which is spherical or oval (See e.g., FIG. 1). The shapes that have been provided in accordance with the present invention are cuboidal, lobate (e.g., asterisk-like or star-like), and geodesic (e.g., multifaceted such as soccer ball-shaped). As the conjugation of metallic colloidal particles to biomolecules depends primarily on adsorption phenomena, each of these shapes presents more surface area for adsorption than similarly sized spherical particles. See, FIGS. 2–5 for micrographs of colloidal shapes in accordance with the present invention.

Particles of the present invention suitably range in size from about 3 nm to about 150 nm. In sufficiently high concentrations, the particles of the present invention are compatible with light microscopy (LM) with each colloidal type providing a different color. Platinum and palladium colloidal particles are dark amber to golden brown. Silver particles range in color from red to purple depending on particle size (e.g., colors include red, orange-red, orange, yellow, green, purple). Rhodium particles are amber or reddish brown to yellow depending on size. Ruthenium particles are light amber or yellow to orange to yellow orange, and molybdenum particles are blue.

In another aspect, the present invention provides a method for making nonspherical colloidal particles of differing elemental composition and differing morphology. The method includes making colloidal particles of a metal selected from the group consisting of silver, palladium, platinum, rhodium, and ruthenium by reducing a solution of a compound of the metal with a reducing agent. The reducing agent suitably includes tannic acid, sodium citrate, ferrous sulfate, ascorbic acid, sodium borohydride, hydrogen, ethanol, methanol or combinations thereof. The incubation period/reaction time for formation of the colloidal particles ranges from virtually instantaneous to 6 hours. The incubation/reaction temperature ranges from 0° C. to 100° C. The initial concentration of the metal compound ranges from about 1 $\mu$M to about 20 mM. The concentration of reducing agent ranges from about 0.1 nM to about 100 mM.

The metal compound is typically a salt, suitably but not limited to a nitrate or a chloride. For example, for cAg, the metal compound is suitably silver nitrate and the reducing agent is sodium citrate/ferrous sulfate. For cPd, the metal compound suitably includes $PdCl_2$, $(NH_4)_2PdCl_4$, or $K_2PdCl_4$, and the reducing agent is preferably ascorbic acid, ascorbic acid/tannic acid, sodium citrate/tannic acid, sodium borohydride or hydrogen. For cPt, the metal compound is suitably $H_2PtCl_4$, and the reducing agent is suitably ascorbic acid, sodium citrate/tannic acid or sodium borohydride. For cRh, the metal compound is suitably $RhCl_3$, and the reducing agent is ascorbic acid. For cRu, the metal compound is suitably $(NH_4)_2RuCl_6$ or $RuCl_3$, and the reducing agent is ascorbic acid.

The colloidal particles of the elemental composition in accordance with the present invention include, in respect of shape, cuboidal, lobate (e.g. asterisk-shaped) or geodesic (e.g., soccer ballshaped), and in respect to size, a range of from about 3 nm to about 500 nm, suitably about 3 nm to about 100 nm, and more preferably about 3 nm to about 18 nm.

Figure 6:
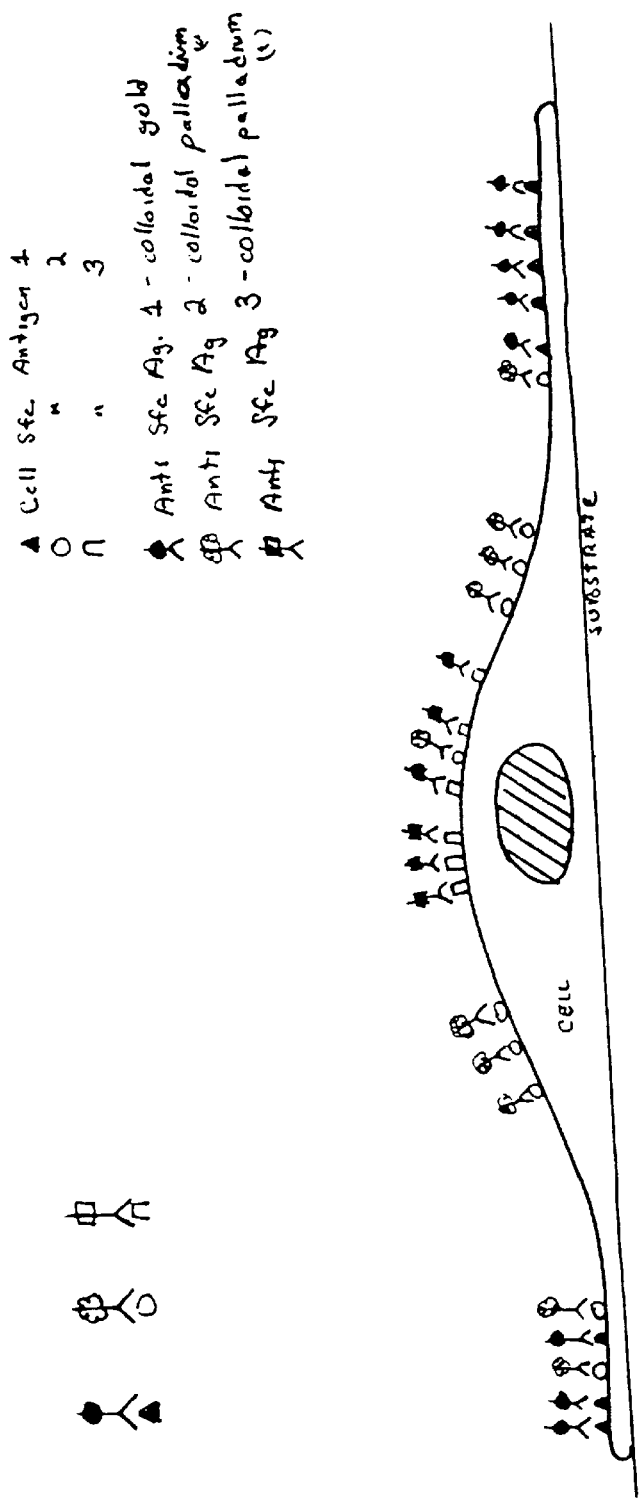
FIG. 6 is a schematic representation of multiple labeling of cell surface molecules utilizing different elemental composition colloidal having different morphologies.

In a further aspect, the invention provides a method of multiple labeling which comprises conjugating to differing biomolecules sought to be labeled colloidal metal particles; each type of biomolecule having a different colloidal particle having differing elemental composition and/or differing morphology from the other types of biomolecules. The colloidal particles are selected from silver, palladium, platinum, rhodium, molybdenum and ruthenium, and the morphologies selected from spherical, cuboidal, lobate or geodesic. The biomolecules to be labeled include but are not limited to antibodies, cells, cellular components, cellular surface molecules, proteins, antigens or fragments thereof. For example, antibodies suitably adsorbed to colloidal particles of the present invention include but are not limited to IgG or Fab fragment thereof; non-antibody proteins include but are not limited to fibrinogen, albumin and insulin. Non-protein molcules suitably include, e.g., Iipopolysacchrides and lectins. The colloidal labels permit visualization and resolution with light microscopy, electron microscopy, x-ray microscopy or force microscopy. FIG. 6 is a schematic representation of multiple labeling for cell surface analysis with conjugates of antisurface antigen and differing colloidal metal with differing shapes.

It has also been found that multiple labeling can also be accomplished based solely on elemental composition using energy filtering transmission electron microscopy (EFTEM). Images generated with zero energy loss electrons are compared to images produced using energy loss electrons at emission maxima and minima for the specific elements. Energy loss maxima and minima are characteristic for each element, and therefore, colloidal metallic particles of differing elemental composition can be readily differentiated from one another in the electron microscope based on their elemental composition rather than on their size or shape. This permits use of multiple labeling procedures with similarly sized particles. Hence, multiple probes with multiple specificities can be simultaneously employed for EFTEM studies. This greatly facilitates co-localization studies at sub-cellular, molecular and sub-molecular levels of resolution. It is also contemplated that colloidal particles composed of two or more elements will have unique electron emission properties and can, hence, provide further distinguishing particles.

All colloidal particles in accordance with the present invention are compatible with existing preparative procedures for chemical or physical (cryo) fixation, staining, solvent dehydration, polymer embedding, thin sectioning, and dehydration by the critical point or freeze drying procedures. The colloidal particles of the present invention in multiple labeling procedures can be utilized for their differing particle shapes or differing elemental composition or both.

In yet another aspect, the invention provides a method of gel staining which comprises staining each species sought to be stained with colloidal metal particles, each species having a different metal with differing particle sizes from the other. The metals include silver, palladium, platinum, rhodium, molybdenum and ruthenium, and the particle size ranges from about 1 nm to about 100 nm. The color staining provided is: platinum—dark amber to golden brown; palladium —darker brown; silver—red to green to purple depending on size from smaller to larger particles; rhodium—red-brown or umber to yellow depending on size from smaller to larger particle; molybdenum—blue; and ruthenium—light umber or yellow.

Figure 7:
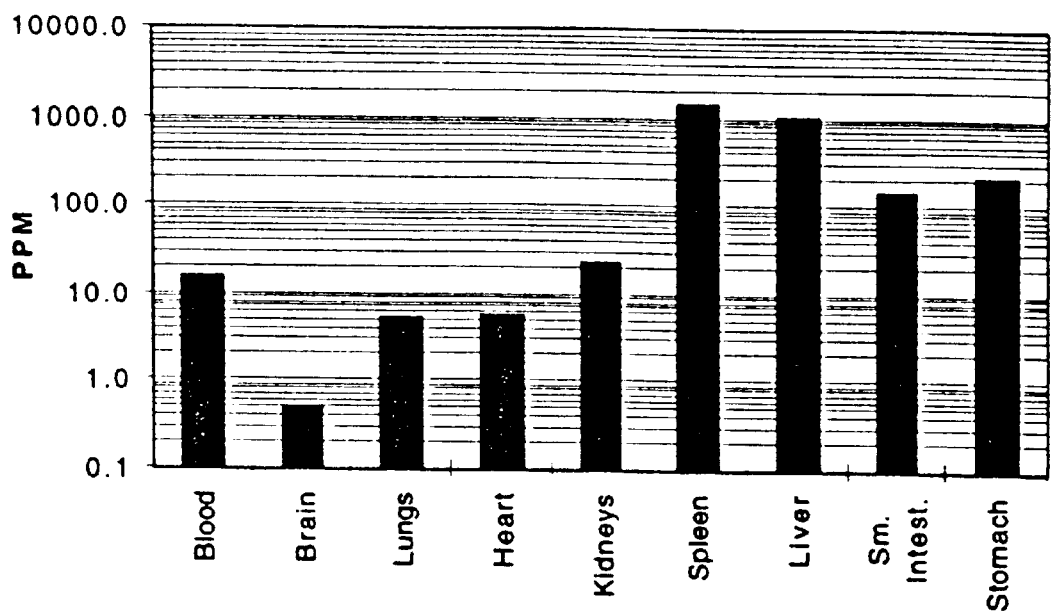
FIG. 7 is a graphical representation of cAu distribution at the organ level of mice injected with 13 nm cAu intermittantly.
Figure 8:
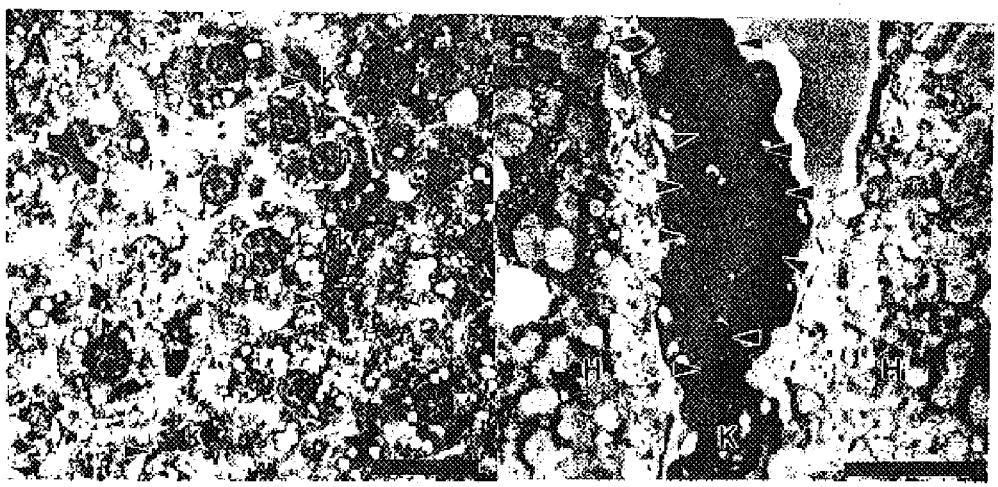
FIG. 8 is an LM(A) and TEM(B) micrographs showing cAu localized primarily in the phagocytic Kupffer cells (K) of the liver with virtually no cAu detected in the heptatocytes (H).

It has been found that colloidal particles in the small size range of about 1 nm to about 50 nm can be absorbed via the intestinal tract and can be detected in substantial amount in various organs including, e.g., the brain, liver, spleen, kidney, as seen graphically represented in FIG. 7 and visualized in the micrograph of FIG. 8. Thus, in yet a further aspect, the invention provides a delivery system for biomolecules or drugs to an in vivo target, which includes providing the colloidal particles of the present invention in particle sizes from about 1 nm to about 80 nm, preferably 1 nm to 50 nm, most preferably less than 4 nm, as carriers for biomolecules or drugs. For example, colloidal gold, cAu, has been found to be suitable with a particle size range from about 1 nm to about 15 nm. Particles of shapes differing from the spherical cAu particles should also have value in the delivery system in accordance with the present invention due to increased surface area and increased potential for binding.

Preferably, the biomolecules sought to be delivered include nucleic acids, proteins or peptides, e.g., an antibody or an antigen. Such metal colloid conjugates are prepared by known methods (see, e.g., R. M. Albrecht et al. in Immunocytochemistry: A Practical Approach, J. E. Beesley ed., Oxford University Press (1993) pp.151–176); U.S. Pat. No. 5,384,165 issued to Kidwell et al.) For example, cAu can be conjugated to virtually any protein by hydrophobic bonding under conditions by which the conjugates retain the properties of the protein. Use of colloidal particles of small size compared to the ligand, e.g., protein, antibody, ensures that the conjugation does not affect the activity or function of the protein.

It has also been found that colloidal metallic labels, e.g., cAu, can be used in tracking and determining the location of the conjugates following in vivo administration. INAA can be used for locating, e.g., gold-conjugated molecules at the tissue or bulk specimen levels, while LM, SEM and TEM can then be used to visualize the location of the conjugates at the cellular and ultrastructural levels. It is preferable that the colloidal metallic particles be smaller than, e.g., protein molecule to which they are conjugated such that the conjugate yields roughly 1 particle per protein molecule. As such, the conjugate size remains close to the size of the protein alone.

The present invention is further explained by the following examples which should not be construed by way of limiting the scope of the present invention.

PREPARATION OF COLLOIDAL PALLADIUM
(cPd)

EXAMPLE 1

A solution of 4 mM palladium chloride ($PdCl_2$) was prepared by dissolving 0.355 g of the salt in a 500 mL aqueous solution of 1% hydrochloric acid. 15.02 g urea was dissolved in 40 mL dd$H_2O$ to yield a 6.02 M solution. The two solutions were combined and incubated at 75° C. to form a palladium chloride/urea stock solution. A 1% solution of L-ascorbic acid was prepared by dissolving 0.4 g in 36 mL ddH$_2$O followed by addition of 4 mL of the palladium chloride/urea stock solution to give a final concentration of 400 µM palladium chloride, 50 mM urea, and 57 mM L-ascorbic acid. This mixture was incubated at 75° C. for 100 minutes during which time a brown colloid formed that consisted of cuboidal particles with a mean diameter of 45.0±14.1 nm. See, e.g., FIG. 2.

4 mL of the palladium chloride/urea solution was also reduced in a final volume of 40 mL 10% (570 mM) L-ascorbic acid and incubated at 75° C. for 100 minutes. This preparation and all subsequent colloids were observed by energy filtering transmission electron microscopy (EFTEM) to determine shape and size.; The preparation yielded particles having a lobate morphology and mean diameter of 26.1±6.6 nm. See, e.g., FIG. 3.

EXAMPLE 2

4 mL of the palladium chloride/urea stock solution, prepared as described previously in Example 1, was diluted ten-fold with 36 mL ddH$_2$O. A solution of reducing agents was prepared by combining 0.8 mL of 1% sodium citrate, 1.0 mL of 1% tannic acid, and 0.02 mL of 250 mM potassium carbonate. This reducing agent solution was then combined with 40 mL of the diluted palladium chloride/urea solution and incubated at 75° C. for 100 minutes. The concentrations of reagents in the combined solution were 382 µM palladium chloride, 48 mM urea, 650 µM potassium carbonate. The resulting colloidal particles had a mean diameter of 50.3±8.0 nm and were spherical or faceted in morphology.

Another solution of reducing agents was prepared by adding together 0.8±mL of 1% sodium citrate, 0.2±mL of 1% tannic acid and 0.02±mL of 250 mM potassium carbonate. This reducing agent solution was combined with 40 mL of diluted palladium chloride/urea solution as described above in this Example, and incubated at 75° C. for 100 minutes. The concentrations of tannic acid and potassium carbonate in this combined solution were 28 µFM and 120 µM, respectively. The particles that were produced by this procedure were spherical or faceted and had a mean diameter of 69.7±10.6 nm.

A third solution of reducing agents as prepared by mixing 0.8 mL of 1% sodium citrate and 0.1 mL of 1% tannic acid. This reducing agent solution was combined with 40 mL of the diluted palladium chloride/urea solution and incubated at 75° C. for 100 minutes. The concentration of tannic acid in this solution was 14 µM, and spherical or faceted particles with a mean diameter of 69.7±10.6 nm were formed.

EXAMPLE 3

0.04 g tannic acid was dissolved in 37.5 mL ddH$_2$O. 2.5 mL of the palladium chloride/urea solution, prepared as described previously in Example 1, was added to the solution of tannic acid to bring the volume of the reaction mixture to 40 mL. The concentrations of reagents in this combined solution were 250 µM palladium chloride, 31 mM urea, and 600 µM tannic acid. Following a 30 minute incubation at 70° C., lobate particles having a mean diameter of 15.9±8 nm were generated.

Unstable colloids resulted when the procedures described in this Example was repeated with the concentration of tannic acid increased to 3 mM, 6 mM, 30 mM, or 60 mM.

EXAMPLE 4

0.4 g potassium tetrachloropalladate (K$_2$PdCl$_4$) was added to 40 mL ddH$_2$O to prepare a 1% stock solution. A 20% stock solution of L-ascorbic acid was prepared by dissolving 8 g in sufficient ddH$_2$O to yield 40 mL. The stock L-ascorbic was then diluted to a 10% solution by adding 10 mL of the stock to an equal volume of ddH$_2$O. To the 10% L-ascorbic acid solution was added 328 µL of the 1% potassium tetrachloropalladate stock solution to yield a reaction mixture consisting of 250 µM potassium tetrachloropalladate and 570 mM L-ascorbic acid. The reaction was carried out at room temperature and a brown colloid consisting of lobate particles having a mean diameter of 49.5±12.9 nm was formed within a few seconds after addition of the palladium salt solution to the L-ascorbic acid solution.

Unstable colloids resulted when the amount of L-ascorbic acid in the reaction mixtures was decreased to 5% (285 mM), 1% (57 mM), 0.1% (5.7 mM), or 0.01% (5700 µM) while maintaining the concentration of potassium tetrachloropalladate at 250 µM. These experiments were also conducted at room temperature.

EXAMPLE 5

40 g of L-ascorbic acid was dissolved in sufficient ddH$_2$O to furnish a 396 mL solution which was heated to 95° C. To the hot L-ascorbic acid solution was added 4 mL of 1% potassium tetrachloropalladate bringing the volume to 400 mL. This combined solution consisted of 300 µM potassium tetrachloropalladate and 570 mM L-ascorbic acid, and was incubated an additional hour at 95° C., resulting in lobate particles with a mean diameter of 40.9±17.9 nm.

EXAMPLE 6

A 5% solution of L-ascorbic acid was prepared by dissolving 2.0 g in sufficient ddH$_2$O to yield a volume of 40 mL. 328 µL of 1% potassium tetrachloropalladate was then added to provide a solution consisting of 285 mM L-ascorbic acid and 250 µM palladium. This combined solution was incubated at 0° C. for one hour in an ice water bath, resulting in a colloid composed of lobate particles with a mean diameter of 49±17.6 nm.

164 µL of 1% potassium tetrachloropalladate was added to 40 mL of 5% L-ascorbic acid to yield a solution containing 125 µM palladium. This solution was also incubated for one hour at 0° C. and generated particles of lobate morphology with a mean diameter of 23.0±5.9 nm. Increasing the length of incubation at 0° C. of additional 40mL solutions of the same composition to six hours resulted in lobate particles with a mean diameter of 19.0±4.5 nm.

When 400 mL solutions consisting of 125 µM palladium tetrachloropalladate and 5% L-ascorbic acid, however, were incubated for five hours at 0° C., the mean particle diameter increased to 33.3±5.9 nm. The morphology of these particles was also lobate.

Incubation of 40 mL solutions of 125 µM palladium in 5% L-ascorbic acid at room temperature or at 60° C. for one hour also yields lobate particles with mean diameters of 31.2±7.7 nm and 36.2±19.6 nm, respectively.

EXAMPLE 7

0.4 g ammonium tetrachloropalladate ([NH$_4$]$_2$PdCl$_4$) was added to prepare a 1% stock solution. A 20% stock solution of L-ascorbic acid was prepared as described in Example 4. 292 µL of the 1% palladium stock was then added to 40mL of 10% L-ascorbic acid that had been preheated to 95° C. The concentrations of the reagents in this combined solution were 250 µM ammonium tetrachloropalladate and 570 mM L-ascorbic acid. A brown colloid formed immediately upon addition of the palladium solution. The preparation was incubated at 95° C. for one hour. This procedure yielded lobate particles with a mean diameter of 40.3±17.0 nm.

Addition of 292 μL of 1% ammonium tetrachloropalladate to 40 mL of a solution containing 5% (285 mM) L-ascorbic acid with incubation at 95° C. for one hour yielded lobate particles having a mean diameter of 25.6±8.3 nm.

Reduction of 292 μL 1% ammonium tetrachloropalladate with 40 mL 1% (57 mM) L-ascorbic acid at room temperature resulted in formation of a brown colloid consisting of lobate particles. The mean particle diameter of this preparation was 31.5±13.8 nm.

EXAMPLE 8

20 mL of a 20% L-ascorbic acid stock solution was diluted with 17.1 mL ddH$_2$O. The volume in this solution was then brought to 40 mL with the addition of 2.9 mL 1% ammonium tetrachloropalladate. The concentrations of L-ascorbic acid and the palladium salt in this sample was 10% (570 mM) and 2.5 mM, respectively. Following incubation at 95° C. for 30 minutes, a brown colloid had developed which consisted of lobate particles having a mean diameter of 39.2±26.0 nm.

Reduction of 25 μM ammonium tetrachloropalladate in 40 mL of a solution containing 10% (570 mM) L-ascorbic acid with heating to 95° C. for 30 minutes did not yield a stable colloid, and further decrease in the concentration of ammonium tetrachloropalladate to 2.5 μM or 250 nM resulted in colloids with insufficient particle density.

EXAMPLE 9

A 4% stock solution of L-ascorbic acid was prepared by adding 1.2 g to 30 mL ddH$_2$O. Three, aliquots of 1% L-ascorbic acid were then prepared by diluting 10 mL of the 4% stock solution each in 30 mL ddH$_2$O. A 0.5% solution of ammonium tetrachloropalladate was prepared by diluting 500 μL of a 1% stock solution in an equal volume of ddH$_2$O. 0.2% ammonium tetrachloropalladate was prepared by adding 200 μL of the 1% stock solution to 800 μL ddH$_2$O. 146 μL of 1%, 0.5%, or 0.2% ammonium tetrachloropalladate was then added to each of the three aliquots of 1% L-ascorbic acid. These solutions contained 125 μM, 62.5 μM, and 12.5 μM ammonium tetrachloropalladate, respectively, and were incubated at 95° C. for 1 hour before being cooled rapidly in an icewater bath. The mean particle diameter of the 125 μM, 62.5 μM, 12.5 μM solutions were 38.5±17.1 nm, 38.0±12.7 nm, and 21.1±7.1 nm, respectively. All three preparations gave rise to particles of lobate morphology.

EXAMPLE 10

4.0 g tannic acid was dissolved in enough ddH$_2$O to prepare 40 mL of a 10% stock solution. 40 μL of the tannic acid stock was then added to 40 mL of a 10% L-ascorbic acid solution. This solution of reducing agents was then heated to 95° C. prior to the addition of 292 μL of 1% ammonium tetrachloropalladate. The combined solution contained 570 mM L-ascorbic acid, 59 μM tannic acid, and 250 μM ammonium tetrachloropalladate, and was incubated an additional hour at 95° C. during which time a brown colloid developed, consisting of lobate particles with a mean diameter of 43.2±21.8 nm.

Increasing the concentration of tannic acid in the reaction mixtures to 0.1% (590 μM), 1.0% (5.9 mM), or 5% (29 mM) while maintaining constant the concentrations of L-ascorbic acid and ammonium tetrachloropalladate with similar incubations at 95° C. gave rise to unstable colloids.

EXAMPLE 11

292 μL of 1% ammonium tetrachloropalladate was added to 40 mL of a solution containing 5% (285 mM) L-ascorbic acid and 0.01% (59 μM) tannic acid preheated to 95° C. This sample was incubated one hour at 95° C. during which time a brown colloid formed. The particles had a lobate morphology and mean diameter of 25.2±9.1 nm.

Unstable colloids developed from similar preparations in which the concentration of tannic acid was increased to 0.1% (590 μM), 1.0% (5.9 mM), or 5% (29 mM) while the concentrations of L-ascorbic acid and ammonium tetrachloropalladate remained constant at 285 mM and 250 μM, respectively. These solutions were also incubated at 95° C. for one hour.

292 μL of 1% ammonium tetrachloropalladate was added to a 40 mL solution of 5% L-ascorbic acid and 0.01% tannic acid. However, this sample was maintained at room temperature throughout the experiment, giving rise to lobate particles with a mean diameter of 39.6±16.0 nm.

EXAMPLE 12

0.038 g sodium borohydride was dissolved in 10 mL ddH$_2$O to prepare a 100 mM stock solution. 292 μL of 1% ammonium tetrachloropalladate was added to 40 mL ddH$_2$O, and this solution was heated to 95° C. 320 μL of the 100 mM sodium borohydride stock solution was then added to the dilute ammonium tetrachloropalladate to prepare a solution consisting of 250 μM ammonium tetrachloropalladate and 800 μM sodium borohydride. The resulting solution was incubated at 95° C. for one hour and yielded a gray colloid consisting of spherical particles with a mean diameter of 72.7±11.2 nm.

The above procedure in this Example was repeated varying the amount of 100 mM sodium borohydride added to the 40 mL solution of 250 μM ammonium tetrachloropalladate. These solutions were also incubated at 95° C. for one hour. Gray colloids consisting of spherical particles formed when the concentration of sodium borohydride was maintained at or below 800 μM. Specifically, reduction of the dilute palladium salt with 400 μM, 200 μM, 100 μM, or 50 μM sodium borohydride resulted in the formation of spherical particles with mean diameters of 72.9±12.6 nm, 88.9±15.3 nm, 92.8±14.9 nm, and 89.2±14.2 nm, respectively. However, the colloids produced by reduction with sodium borohydride in excess of 1.6 mM were not stable, with particles settling out of suspension during incubation.

EXAMPLE 13

328 μL of the 1% potassium tetrachloropalladate stock solution was diluted in 37.4 mL ddH$_2$O, and the volume was brought up to 40 mL with the addition of 2.6 mL of the 100 mM sodium borohydride stock solution. The concentrations of reagents in this preparation were 250 μM potassium tetrachloropalladate and 6.4 mM sodium borohydride. The solution was then incubated one hour at 95° C. to produce a gray colloid with spherical particles having a mean diameter of 11.2 ±5.2 nm.

Reduction of 250 μM potassium tetrachloropalladate with greater or lesser concentrations of sodium borohydride did not result in the formation of stable colloids following one hour incubations at 95° C. The concentrations of sodium borohydride tested ranged from 50 µM to 3.2 mM, and from 12.8 mM to 25.6 mM.

EXAMPLE 14

250 µM solutions of ammonium or potassium tetrachloropalladate were prepared by diluting 292 µL of the 1% ammonium salt solution or 328 µL of the 1% potassium salt stock solution with 40 mL ddH2O. A saturated phosphorous solution was prepared in ether and then diluted five-fold by adding 400 µL of the saturated solution to 1.6 mL ether. 333 µL of the dilute phosphorous solution was then added to 40 mL of each of the 250 µM palladium salt solutions, which were then incubated at 95° C. for 30 minutes. This method failed to produce stable palladium colloids.

EXAMPLE 15

413 µL of 1% ammonium tetrachloropalladate was diluted in 120 mL ddH$_2$O in a round bottom glass flask to prepare a 120 µM solution which was then heated to 95° C. A rubber stopper fitted with inlet and exhaust tubing was placed over the mouth of the flask. The inlet tubing extended beneath the surface of the liquid within the flask and the outside portion was connected to a hydrogen gas cylinder. Hydrogen was bubbled through the palladium solution at a pressure of 20 psi for 5 minutes to expel the air in the flask before the exhaust vent was closed, ensuring a pressurized hydrogen atmosphere during the remainder of the reduction process. The inlet valve was then closed and the flask was incubated under a hydrogen atmosphere an additional 30 minutes at 95° C. This method generated a colloid consisting of spherical particles with a mean diameter of 23.7±7.1 nm.

PREPARATION OF COLLOIDAL PLATINUM (cPt)

EXAMPLE 16

A 0.01% stock solution of hydrogen hexachloroplatinate (H$_2$PtCl$_6$) was prepared by dissolving 0.02 g in 200 mL ddH$_2$O. A mixture of 2 mL 1% tannic acid, 0.8 mL 1% sodium citrate, and 0.2 mL of 250 mM potassium carbonate was added to 37 mL of the 0.01% platinum stock to prepare a solution consisting of 244 µM hydrogen hexachloroplatinate, 680 µM sodium citrate, 294 µM tannic acid, and 1.25 mM potassium carbonate. The solution was maintained at room temperature throughout the experiment, and a brown colloid consisting of spherical particles with a mean diameter of 38.5±6.9 nm was formed.

Similar platinum colloids were made in 40 mL aliquots using decreased volumes of 1% tannic acid and potassium carbonate along with commensurately increased volumes of 0.01% hydrogen hexachloroplatinate. All were maintained at room temperature and gave rise to particles having a spherical morphology. A solution containing 232 µM hydrogen hexachloroplatinate, 680 µM sodium citrate, 147 µM tannic acid, and 625 µM potassium carbonate yielded particles with a mean diameter of 33.8±6.9 nm. A solution consisting of 236 µM hydrogen hexachloroplatinate, 680 µM sodium citrate, 73 µM tannic acid and 312 µM potassium carbonate resulted in particles with a mean diameter of 36.7±6.7 nm. Particles having a mean diameter of 47.5±7.9 nm were produced from a mixture of 237 µM hydrogen hexachloroplatinate, 680 µM sodium citrate, 37 µM tannic acid, and 156 µM potassium carbonate, and particles with a mean diameter of 35.4±6.7 nm resulted from a solution of 239 µM hydrogen hexachloroplatinate, 680 µM sodium citrate, and 18 µM tannic acid, but lacking potassium carbonate.

EXAMPLE 17

A 100 mM stock solution of sodium borohydride was prepared as described in Example 12. Several samples of cPt were prepared at room temperature using varying concentrations of the sodium borohydride stock solution. An unstable colloid resulted from the addition of 320 µL of the 100 mM stock to a 40 mL solution of 0.01% (244 µM) hydrogen hexachloroplatinate. The concentration of sodium borohydride in this solution was 800 µM. Similar solutions containing 400 µM sodium borohydride yielded spherical particles with a mean diameter of 34.6±8.9 nm. Decreasing the concentration of sodium borohydride used in these solutions to 200 µM, 100 µM, or 50 µM also resulted in spherical particles having mean diameters of 32.5±6.6 nm, 37.1±7.1 nm, and 39.4±6.5 nm, respectively.

EXAMPLE 18

A 1% stock solution of hydrogen hexachloroplatinate was prepared by adding 0.04 g to 40 mL ddH$_2$O. 4 g L-ascorbic acid was dissolved in sufficient ddH$_2$O to attain a volume of 39.5 mL. 520 µL of the 1% hydrogen hexachloroplatinate stock was added to the L-ascorbic acid solution. The concentrations of L-ascorbic acid and the platinum salt in this solution were 570 mM and 250 µM, respectively. This solution was incubated at 70° C. for 30 minutes, giving rise to lobate particles with a mean diameter of 19.0±±6.6 nm.

Similar samples of cPt were prepared by reducing 250 µM hydrogen hexachloroplatinate with lesser concentrations of L-ascorbic acid. Reduction of a 40 mL aliquot containing 285 mM L-ascorbic acid produced irregularly-shaped particles with a mean diameter of 3.4±1.2 nm following a half-hour incubation at 70° C. A colloid consisting of particles with irregular morphology was also prepared using 57 mM L-ascorbic acid. This solution was also incubated at 70° C. for 30 minutes and the mean particle diameter was 9.1±2.1 nm.

PREPARATION OF COLLOIDAL RHODIUM (cRh)

EXAMPLE 19

A stock solution of 20% L-ascorbic acid was prepared as described in Example 4. 0.4 g rhodium chloride (RhCl$_3$) was dissolved in 40 mL ddH$_2$O to yield a 1% stock solution. A working solution consisting of 10% L-ascorbic acid was prepared by diluting 20 mL of the stock with an equal volume of ddH$_2$O. To this solution was added 258 µL of 1% rhodium chloride, resulting in a solution that consisted of 570 mM L-ascorbic acid and 300 µM rhodium chloride. This solution was then incubated at 95° C. for 1 hour and generated lobate particles with a mean diameter of 14.7±7.1 nm.

Additional samples of cRh were made similarly by preparing 40 mL solutions of 30 µM rhodium chloride in higher dilutions of L-ascorbic acid followed by incubation of the samples at 95° C. for 1 hour. Reduction of 300 µM rhodium chloride with 5% (285 mM) L-ascorbic acid led to the formation of lobate particles with a mean diameter of 17.1±5.7 nm. Decreasing the concentration of L-ascorbic acid to 1% (57 mM) resulted in particles with a mean diameter of 28.1±10.5 nm, also with lobate morphology. However, when the concentration of L-ascorbic acid was decreased further to 0.01% (5.7 mM) or 0.1% (570 µM), an insufficient number of rhodium particles were formed.

EXAMPLE 20

258 µL of the 1% rhodium chloride stock solution was added to 40 mL of an aqueous solution consisting of 50% methanol. The resulting solution, containing 300 µM rhodium chloride, was incubated at 85° C. for 5 hours to generate lobate particles with a mean diameter of 34.1±11.6 nm.

0.04 g polyvinyl alcohol (PVA, MW=10,000) was dissolved in a 40 mL solution consisting of equal volumes of $ddH_2O$ and methanol to which 258 µL of the 1% rhodium chloride stock solution was added. The concentrations of PVA and the rhodium salt in this solution were 0.01% and 300 µM, respectively, and lobate particles having a mean diameter of 19.1±6.6 nm were generated.

PREPARATION OF COLLOIDAL RUTHENIUM (cRu)

EXAMPLE 21

A 20% stock solution of L-ascorbic acid was prepared as previously described in Example 4, and 0.4 g ammonium hexachlororuthenate ($[NH_4]_2RuCl_6$) was added to 400 mL $ddH_2O$ in order to prepare a 0.1% stock solution. 250 µM ammonium hexachlororuthenate was reduced with a final concentration of 5% (285 mM) L-ascorbic acid by diluting 20 mL of the 20% L-ascorbic acid stock with 16.5 mL $ddH_2O$ and then combining this solution with 3.5 mL of the 0.1% ammonium hexachlororuthenate stock. This preparation was incubated at 95° C. for 1 hour during which time a colloid formed which consisted of spherical particles having a mean diameter of 5.4±1.9 nm.

Similar 40 mL samples were prepared in which the concentration of ammonium hexachlororuthenate was maintained at 250 µM but the consideration of L-ascorbic acid was altered. However, too few particles formed following incubation of solutions containing 10% (570 mM), 1% (57 mM), 0.1% (5.7 mM), or 0.01% (570 µM) L-ascorbic acid.

EXAMPLE 22

0.002 g ruthenium chloride hydrate ($RuCl_3.3H_2O$) was dissolved in 100 mL $ddH_2O$ in a round bottom glass flask. This solution, consisting of 96 µM ruthenium was then heated to 95° C. A rubber stopper fitted with inlet and exhaust tubing was placed over the mouth of the flask and hydrogen gas was bubbled through the solution for 5 minutes at a pressure of 20 psi in order to expel the air within the flask. The exhaust and inlet valves were then closed and the flask was incubated under a hydrogen atmosphere an additional 10 minutes at 95° C. The colloid that formed was not stable, consisting of large aggregates of particles. Increasing the length of time that the solution was incubated under hydrogen to 15 or 30 minutes also resulted in unstable colloids, as did a 30 minute incubation under a hydrogen atmosphere at room temperature.

PREPARATION OF COLLOIDAL SILVER (cAg)

EXAMPLE 23

A 6.0 mL solution of reducing agents, which was prepared by combining 3.5 mL 4% sodium citrate dihydrate sodium citrate) and 2.5 mL 3% ferrous sulfate heptahydrate ($FeSO_4.7H_2O$) was added to a 2.5 mL solution of 1% silver nitrate ($AgNO_3$). The concentrations of reagents in this mixture were 17 mM silver nitrate, 56 mM sodium citrate, and 32 mM ferrous sulfate, and all solutions were maintained at room temperature throughout the experiment. Formation of cAg was instantaneous upon the mixture of the silver nitrate with the reducing agents, as indicated by a color change to red-orange. The resultant colloid was observed by energy filtering transmission electron microscopy (EFTEM) and consisted of spherical particles with a mean diameter of 23.2±12.6 nm.

EXAMPLE 24

7.5 mL of the cAg prepared following the procedure described under Example 23 was centrifuged at 100,000 g for 75 minutes in order to pellet the silver particles, following which the supernatant was withdrawn and replaced with 5.0 mL $ddH_2O$. The resuspended colloid was then peptized by the addition of 5.0 mL 4% sodium citrate. The concentration of sodium citrate in the final mixture was 68 mM, and all solutions were maintained at room temperature throughout the experiment. The resultant particles were spherical with a mean diameter of 8.8±4.0 nm.

The procedure described above in this Example was repeated three additional times without appreciable decrease in particle size. Following the second peptization, the mean particle diameter was 8.1±2.7 nm, 8.8±3.6 nm following the third peptization, and 6.1±1.2 nm following the final peptization.

EXAMPLE 25

2.5 mL of a 1% silver nitrate stock solution was diluted with 80 mL $ddH_2O$ and heated to 60° C. The solution of reducing agents was prepared by combining 7.0 mL 4% sodium citrate and 5.0 mL 3% ferrous sulfate. 6.0 mL of the combined reducing agents was diluted with 11.5 mL $ddH_2O$, then added to the silver nitrate solution to give a final reaction volume of 100 mL. The concentrations of reagents in this solution were 1.5 mM silver nitrate, 4.8 mM sodium citrate, and 2.7 mM ferrous sulfate. Formation of cAg was instantaneous upon addition of the reducing agents to the silver nitrate solution, yielding spherical particles with a mean diameter of 8.8±3.6 nm.

EXAMPLE 26

1.5 mL $ddH_2O$ was added to 2.5 mL of the 1% silver nitrate stock and a solution of reducing agents was prepared by combining 7.0 mL 4% sodium citrate and 5.0 mL 3% ferrous sulfate. 6.0 mL of the combined reducing agents was added to the silver nitrate solution to give a final volume of 10 mL with reagent concentrations of 15 mM silver nitrate, 48 mM sodium citrate, and 27 mM ferrous sulfate. The reaction mixture was maintained at room temperature for the duration of the experiment and generated a red-orange colloid consisting of spherical particles with a mean diameter of 6.1±1.2 nm.

9.0 mL of this preparation was centrifuged at 100,000 g to pellet the silver particles as described previously in Example 24. The pellet was resuspended in 5.0 mL $ddH_2O$ to reconstitute the colloid, followed by peptization of the particles by the addition of 5.0 mL 4% sodium citrate. This procedure resulted in an unstable colloid in which the particles settled out of suspension.

EXAMPLE 27

170 µL of a 1% silver nitrate solution was diluted in 40 mL $ddH_2O$. The reducing agents solution was prepared by combining 7.0 mL 4% sodium citrate and 5.0 mL 3% ferrous sulfate. 100 µL of the reducing agents was added to the dilute silver nitrate and the mixture was incubated at 95° C. for 1 hour. The concentrations of reagents in this solution was 250 $\mu$M silver nitrate, 198 $\mu$M sodium citrate and 112 $\mu$M ferrous sulfate. The colloid consisted of spherical particles with a mean diameter of 16.4±4.8 nm.

Additional silver colloids were prepared following the method described in this Example with the exception that the volume of reducing agents added to the dilute silver nitrate solutions was varied. Spherical particles resulted in all of these preparations. Addition of 200 $\mu$L of the reducing agents (final concentrations of 397 $\mu$M sodium citrate and 225 $\mu$M ferrous sulfate) resulted in particles with a mean diameter of 8.7±2.2 nm. Addition of 400 $\mu$L of the reducing agents (793 $\mu$sodium citrate and 450 $\mu$M ferrous sulfate) yielded particles with a mean diameter of 15.6±3.7 nm.

The concentrations of sodium citrate and ferrous sulfate used to reduce 250 $\mu$M silver nitrate greatly influence the color of the resulting sol. Solutions containing between 99 $\mu$M and 1.59 mM sodium citrate with between 56 $\mu$and 899 $\mu$M ferrous sulfate (50 $\mu$L to 800 $\mu$L of the reducing agents stock solution added to 40 mL dilute silver nitrate) are initially orange-red in color with no Tyndall effect. After aging for several weeks, however, the color of each solution changes depending upon the concentration of reducing agents added and a pronounced Tyndall effect is observed. Solutions containing 99 $\mu$M to 397 $\mu$M sodium citrate with 56 $\mu$M to 225 $\mu$M ferrous sulfate (50 $\mu$L to 200 $\mu$L of the reducing agents stock added to 40 mL dilute silver nitrate) are olive drab in color to reflected light but violet to transmitted light. Solutions containing 793 $\mu$M to 1.59 mM sodium citrate with 450 $\mu$M to 899 $\mu$ferrous sulfate (400 $\mu$L to 800 $\mu$L of the reducing agents stock added to 40 mL dilute silver nitrate) are dark blue in color to reflected light, and to transmitted light are orange-red at the lower concentrations of sodium citrate/ferrous sulfate and red at the higher concentrations.

Absorption and Distribution of Small Colloidal Particles in vivo

EXAMPLE 28

A. Preparation of Colloidal Particles

Colloidal gold suspensions were prepared by reducing gold chloride (HAuCl$_4$) with sodium citrate or sodium citrate and tannic acid as described in Example 2 with modification to yield a 10-fold concentration (see,also, Albrecht et al., Immunocytochemistry: A Practical Approach, (Beesley, J. E. (ed.), Oxford University Press, New York, pp. 151–176) To make concentrated colloidal gold suspensions, 2.5% maltodextrin was added to the solution as a stabilizer prior to gold chloride reduction to prevent bead auto-aggregation.

To determine colloidal gold particle diameters, suspensions were viewed by transmission electron microscopy using a Philips CM 120 STEM running on TEM mode at 80 keV accelerating voltage. TEM negatives of the suspension were digitized and imported into Metamorph® Imaging System software (Universal Imaging Corporation, West Chester, Pa.) on a DataStor Pentium Pro 200 MHz. One hundred beads were then measured and statistics calculated. Distance calibration was done using the negatives's scale bar. Colloidal gold particle diameters in the four colloidal gold suspensions made were measured at 4≅0.8 nm, 10±2 nm, 28±8 nm, and 80±29 nm, respectively.

B. Colloid Administration

BALB/c mice were injected with 1 mL of 10×13 nm colloidal gold IP Every day for 4 days. The animals were sacrificed by dislocation of the cervical vertebrae under ether anesthesia, either three days or three hours following the final injection. Blood, brain, lung, heart, kidney, spleen, liver, small intestine and stomach samples were then collected for analysis by instrumental neutron activation analysis (INAA), LM and TEM.

C. Quantification of Colloidal Particles by INAA

Figure 2:
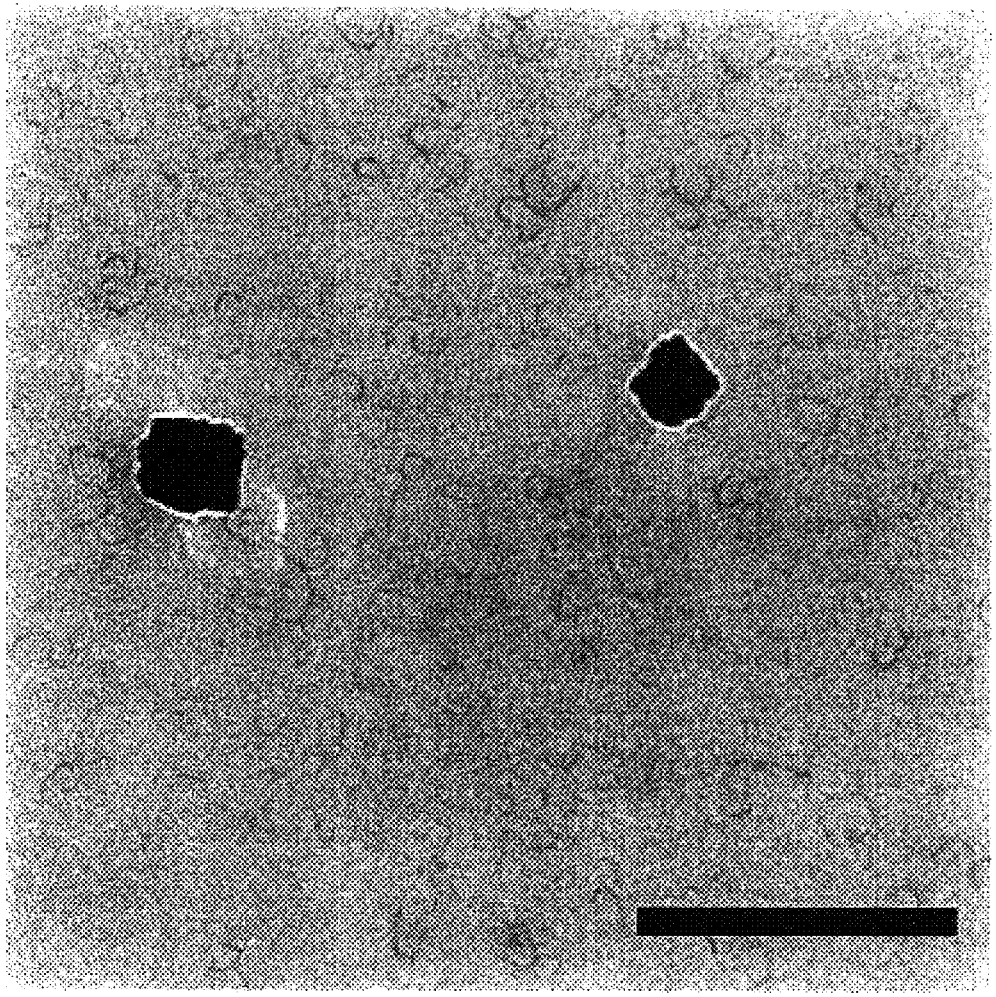
FIG. 2 is a TEM micrograph of cuboidal cPd particles.
Figure 3:
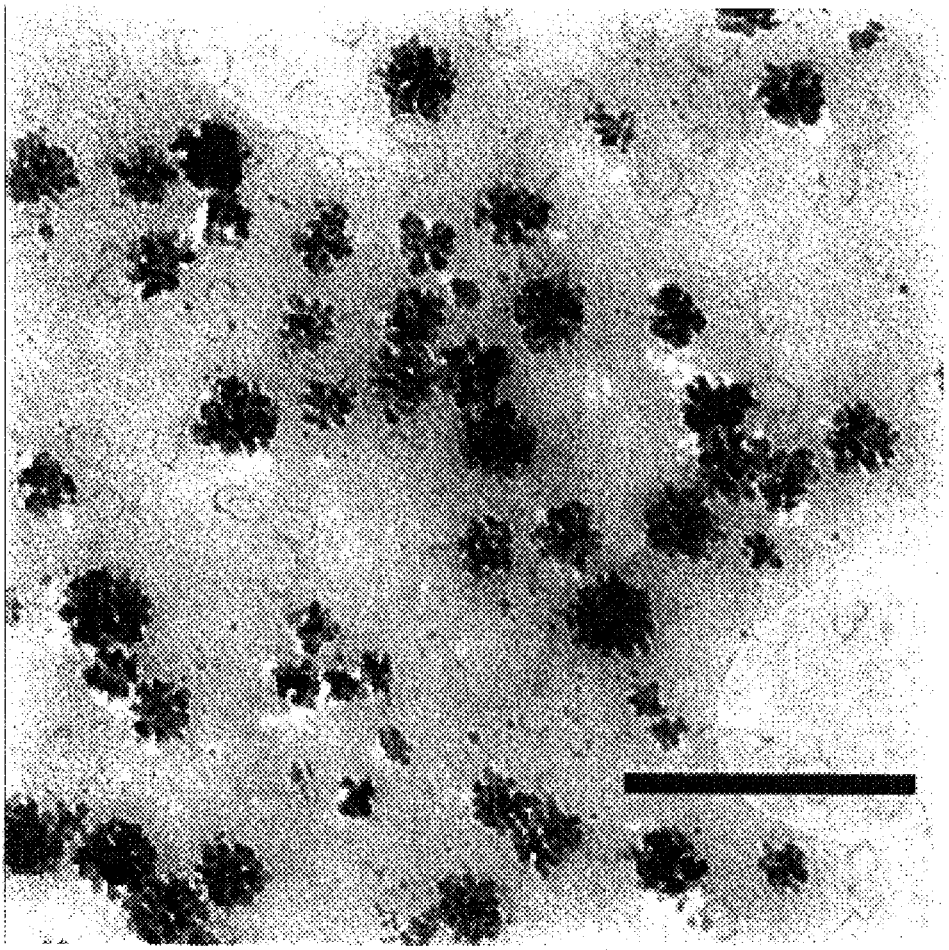
FIG. 3 is a TEM micrograph of lobate cPd particles.
Figure 4:
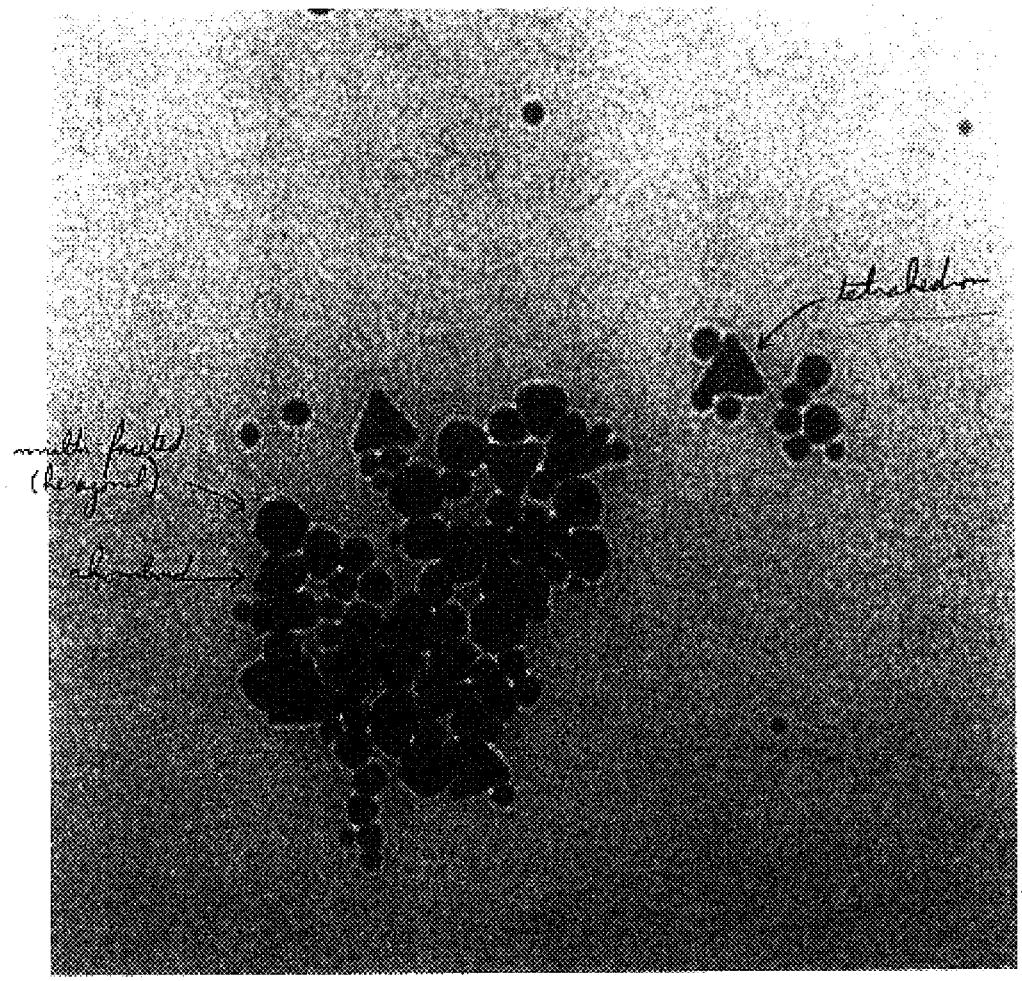
FIG. 4 is a TEM micrograph of faceted cAu particles.
Figure 5:
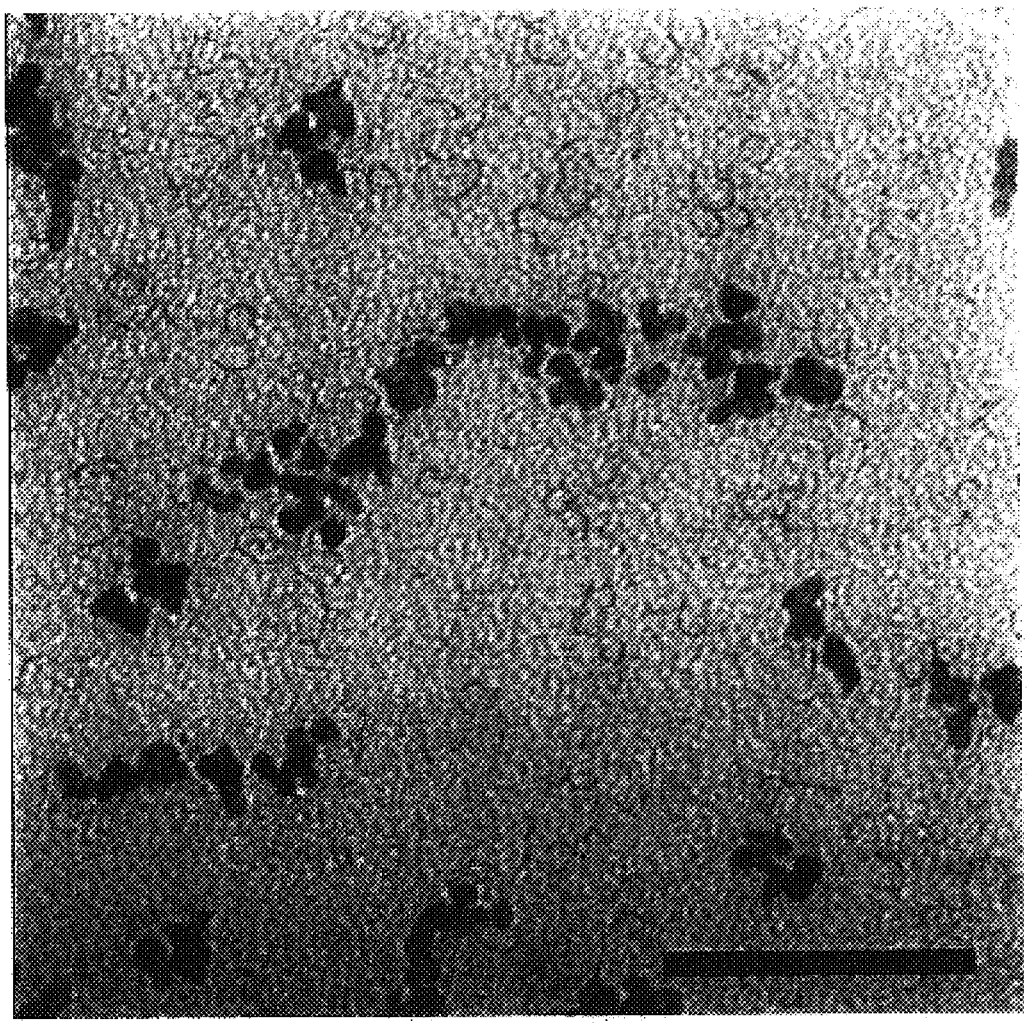
FIG. 5 is a TEM micrograph of irregular-shaped cPt particles.

INAA was used to quantitate the amount of gold at the organ and tissue levels. Representative portions of tissues of experimental and normal (control) animals were collected and placed in trace element-free ⅖ dram polyethylene flip-top vials. Samples were sealed by friction welding and exposed for 7200 second while rotating to a thermal neutron flux of 1×10$^{13}$ neutron/cm$^2$ sec using a 1 MW TRIGA open pool reactor at the University of Wisconsin Madison Nuclear Reactor Laboratory, triggering the conversion of $^{197}$Au to $^{198}$Au. Starting 6.3 days after neutron bombardment, the γ-rays emitted by the samples were counted and sorted by energies using an Ortec intrinsic germanium detector coupled to a PC-based multichannel γ-ray spectrometer using an Oxford PCA-II MCA board. Photopeaks and counts were converted to saturation with correction for dead time, interfering γ-rays and radioactive decay. Gold standards of 5 $\mu$g were run with the experimental samples to standardize a library of gold element data from which the amount of gold present in the unknowns was calculated. Background levels were determined by irradiating untreated tissue samples of similar size and composition to that of experimental samples since detection limits by INAA are dependent on sample composition. Background levels were reduced by allowing samples to decay for 7.5 days after irradiation and prior to counting to decrease the radioactivity levels of shorter lived radionuclides that contribute considerably to the Compton continuum background, thus making radioactivity of longer lived radionuclides prominent even when found in much lower quantities. Final gold values were calculated by averaging the gold concentration in the corresponding organs of 3 different experimental mice minus the average gold concentrations in the respective organs of 2 control mice to correct for background gold levels in tissues and sample vials. Results of particle distribution and micrographs of organs are shown in FIGS. 2 and 3, respectively.

Gold concentrations using other sized particles were found in the various organs as follows: blood—6.83 PPB (parts per billion, ng$_{Au}$/g$_{tissue}$) for 4 nm particles, 0.77 PPB for 10 nm particles, 0.47 PPB for 28 nm particles and −0.09 PPB for 80 nm particles; brain—32.42 PPB for 4 nm particles, 2.06 for 10 nm particles, 0.70 PPB for 28 nm particles and 2.40 PPB for 80 nm particles; lung—75.40 PPB for 4 nm particles, 8.55 PPB for 10 nm particles, 0.80 PPB for 28 nm particles and −0.43 PPB for 80 nm particles; heart—75.40 PPB for 4 nm particles, 8.55 PPB for 10 nm particles, 0.80 PPB for 28 nm particles and −0.43 PPB for 80 nm particles; kidneys—22.44 PPB for 4 nm particles, 17.36 PPB for 10 nm particles, 6.19 PPB for 28 nm particles and 1.46 PPB for 80 nm particles; spleen—38.83 PPB for 4 nm particles, 7.01 PPB for 10 nm particles, 13.74 PPB for 28 nm particles and −0.65 PPB for 80 nm particles; liver—4.67 PPB for 4 nm particles, 2.78 PPB for 10 nm particles, 1.16 PPB for 28 nm particles and 0.37 PPB for 80 nm particles.

These results demonstrated cAu nanoparticles are absorbed in various organs including the brain. The amount of absorption decreases generally with increasing nanoparticle size. Nanoparticles, e.g. 4 nm or smaller, have potential use to deliver molecules to the brain.

PREPARATION OF COLLOIDAL PALLADIUM AND PLATINUM-PROTIEN CONJUGATES

EXAMPLE 29

A. General Preparatory Method

1. Preparation of Metal Colloids

Colloidal palladium (cPd) and colloidal platinum (cPt) are prepared by the ascorbic acid method described above. Unreacted L-ascorbic acid, which is used in the preparation of colloidal palladium (cPd) and platinum (cPt), interferes with protein adsorption to the metal particles and must be removed prior to introduction of the protein. The colloidal particles are first pelleted by ultracentrifugation. The supernatant is then withdrawn and the pellet is resuspended in $ddH_2O$ to about half the original volume. Residual L-ascorbic acid is removed by dialysis of the resuspended colloid against a 5 mM buffer solution with several changes to fresh buffer every 30 minutes until the colloid has attained the pH of the buffer. Colloid/protein conjugates are most stable when the protein has bound to the metal particles by a combination of hydrophobic interactions, Van der Waal's forces of attraction, and London dispersion forces rather than by electrostatic interaction. Proteins are most hydrophobic and bind most stably to colloidal particles near their isoelctric points ($P_i$). Consequently, the pH of the buffer solutions against which the palladium and platinum colloids are dialyzed is adjusted slightly basic to the $P_i$ of the protein to be adsorbed. For example, cPd and cPt are dialyzed against 5 mM 2-[N-morpholino]ethanesulfonic acid (MES) at pH 5.8 for adsorption of protein A, and against 5 mM tris[hydroxymethyl]aminomethane (Tris) at pH 7.2 for adsorption of fibrinogen (Fgn) or immunoglobulin antibodies (Ig).

2. Determination of Protein Concentration Isotherm

The minimal concentration at which various proteins stabilize colloidal particles against electrolyte-induced flocculation is determined by means of a protein concentration isotherm. Small aliquots of cPd or cPt are added to one-tenth the volume of protein in each sample of a linear dilution series which typically ranges in concentration by a factor of 10 to 100 from lowest to highest. After the samples have been mixed, approximately one-tenth the volume of a saturated sodium chloride solution is added to each. Unprotected colloids remain stable by electrostatic repulsion due to a shell of anions surrounding each particle. Addition of the electrolyte collapses this anionic shell and promotes aggregation and precipitation of the particles. Proteins adsorbed to the surface of the metallic particles protect the colloid against electrolytically-induced flocculation. The optimum concentration of protein to be conjugated to the metal particles is determined by the minimal concentration of protein required to prevent precipitation of the particles as determined by the isotherm.

B. Preparation of cPd-Fgn Conjugate

The optimal concentration of Fgn to stabilize 25 nm cPd was determined by isotherm analysis to be 13 μg per mL of colloid. 30 mL 25 nm cPd was added to 3 mL of 130 μg/mL Fgn in HEPES-Tyrodes buffer, pH 7.3. 3 mL 12% maltodextrin in buffer was added to the cPd/Fgn to attain a final concentration of 1%. Maltodextrin acts as a secondary stabilizer, preventing the conjugates from adhering to the surface of the centrifuge tubes. The preparation was then mixed by inversion and ultracentrifuged to pellet the conjugates. The supernatant was removed and replaced with 300 μL buffer to attain a particle density of approximately $5 \times 10^{12}$/mL which is optimal for cell surface labeling.

Given that the colloidal particles of the present invention can be made in very small sizes, that they can be readily conjugated to biomolecules, such as proteins or genetic material by noncovalent interactions that do not affect the conformation or activity of the molecule, that particles can be attached to an absorption enhancer or targeting molecule as well as molecule to be delivered, that colloidal particles are not biodegradable, and that particles that are small enough are readily absorbed through the gut, colloidal particles in accordance with the present invention are of potential value for a carrier system for the oral and parental delivery of molecules.

In summary, the present invention provides colloidal particles of differing elemental composition and morphologies than the prior art colloidal gold. The colloidal particles can be made in particle size from 1 nm to 500 nm and the differing shapes provide more surface area for conjugation and adsorption than the spherical gold particles. The colloidal particles can be used for multiple labeling procedures, for gel staining techniques and the smallest sizes, e.g., 4 nm or less, have greatest potential as a drug or biomolecule delivery system.

While the present invention has now been described and exemplified with some specificity, those skilled in the art will appreciate the various modifications, including variations, additions and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method of making nonspherical colloidal particles of a size ranging from 1 to 70 nm, of a metal selected from the group consisting of palladium, platinum, rhodium, and molybdenum which comprises reducing a solution of a compound of the metal with a reducing agent selected from the group consisting of tannic acid, sodium citrate, ferrous sulfate, ascorbic acid, sodium borohydride, hydrogen, ethanol, methanol and combinations thereof, wherein the particle has a shape which is cuboidal, lobate or geodesic.

2. The method of claim 1 wherein the reducing step has an incubation period/reaction time ranging from instantaneous to 6 hours.

3. The method of claim 1 where the reducing step is conducted with a reaction temperature ranging from 0° C. to 100° C.

4. The method of claim 1 wherein the compound the metal has an initial concentration of the metal compound ranging from 1 μM to 20 mM.

5. The method of claim 1 wherein the reducing agent has a concentration ranging from 0.1 to 100 mM.

6. The method of claim 1 wherein the compound of the metal is a nitrate or a chloride.

7. The method of claim 1 wherein the metal is palladium, the compound of the metal is selected from the group consisting of $PdCl_2$, $(NH_4)_2PdCl_4$, and $K_2PdCl_4$, and the reducing agent is selected from the group consisting of ascorbic acid, ascorbic acid/tannic acid, sodium citrate/tannic acid, sodium borohydride and hydrogen.

8. The method of claim 1 wherein the metal is platinum, the metal compound is $H_2PtCl_4$, and the reducing agent is selected from the group consisting of ascorbic acid, sodium citrate/tannic acid and sodium borohydride.

9. A method of making nonspherical colloidal particles of rhodium which comprises reducing a solution of $RhCl_3$ with ascorbic acid.

10. The method of claim 1 wherein the nonspherical colloidal particles have a shape which is cuboidal.

11. The method of claim 1 wherein the nonspherical colloidal particles have a shape which is lobate.

12. The method of claim 1 wherein the nonspherical colloidal particles have a shape which is geodesic.

13. The method of claim 1 wherein the nonspherical colloidal particles are of a size from 3 nm to 12 nm.

14. The method of claim 1 wherein the metal is selected from the group consisting of platinum, rhodium, and molybdenum.

* * * * *